(12) United States Patent
Cho et al.

(10) Patent No.: US 11,820,967 B2
(45) Date of Patent: Nov. 21, 2023

(54) HANGING DROP DEVICE, FORMATION METHOD OF HANGING DROP AND CELL CULTURE METHOD BY USING HANGING DROP

(71) Applicant: NATIONAL TSING HUA UNIVERSITY, Hsinchu (TW)

(72) Inventors: Chin-Yi Cho, Hsinchu (TW); Jen-Huang Huang, Hsinchu (TW); Tzu-Hsiang Chiang, Hsinchu (TW)

(73) Assignee: NATIONAL TSING HUA UNIVERSITY, Hsinchu (TW)

( * ) Notice: Subject to any disclaimer, the term of this patent is extended or adjusted under 35 U.S.C. 154(b) by 80 days.

(21) Appl. No.: 17/308,154

(22) Filed: May 5, 2021

(65) Prior Publication Data
US 2022/0267707 A1 Aug. 25, 2022

(30) Foreign Application Priority Data
Feb. 25, 2021 (TW) ................. 110106799

(51) Int. Cl.
C12M 1/12 (2006.01)
C12M 1/32 (2006.01)
C12M 1/00 (2006.01)
C12M 1/26 (2006.01)
C12N 5/00 (2006.01)

(52) U.S. Cl.
CPC ............ *C12M 25/01* (2013.01); *C12M 23/12* (2013.01); *C12M 23/38* (2013.01); *C12M 25/06* (2013.01); *C12M 33/12* (2013.01); *C12N 5/0062* (2013.01); *C12N 2513/00* (2013.01)

(58) Field of Classification Search
CPC ...... C12M 25/01; C12M 23/12; C12M 23/38; C12M 25/06; C12M 33/12; C12N 5/0062; C12N 2513/00
See application file for complete search history.

(56) References Cited

U.S. PATENT DOCUMENTS

| 10,683,477 | B2 * | 6/2020 | Sumi | C12M 47/02 |
| 2011/0306122 | A1 * | 12/2011 | Moritz | B01L 3/5085 |
| | | | | 435/325 |
| 2016/0108352 | A1 | 4/2016 | Zimmermann et al. | |

FOREIGN PATENT DOCUMENTS

| CN | 102947710 A | 2/2013 |
| CN | 103429729 A | 12/2013 |
| WO | 2013/049165 A1 | 4/2013 |

OTHER PUBLICATIONS

Teo et al (Negative Pressure Induced Droplet Generation in a Microfluidic Flow-Focusing Device. Anal. Chem. vol. 89, Feb. 2017). (Year: 2017).*
Drip tray (ebay, 53x40cm drip tray with pouring spout) (Year: 2022).*
Culture system (Thermo Scientific Nunc EasyFill CellFactor Systems). (Year: 2018).*
Chin-Yi Cho et al., "Development of a Novel Hanging Drop Platform for Engineering Controllable 3D Microenvironments", Frontiers in Cell and Developmental Biology, published on May 7, 2020, vol. 8, article 327, pp. 1-11, published by Frontiers Media S.A., Switzerland.

* cited by examiner

*Primary Examiner* — Kara D Johnson
*Assistant Examiner* — Matasha Dhar
(74) *Attorney, Agent, or Firm* — Lippes Mathias LLP

(57) ABSTRACT

A hanging drop device is provided in the present disclosure. The hanging drop device includes a hanging drop box and a negative pressure module. The hanging drop box includes a plate and a cover. The cover is coupled with the plate to jointly delimit a pressure chamber. The cover includes an upper surface and a bottom surface, a plurality of wells are recessed from the upper surface, and each of the wells is communicated with the pressure chamber through a hole. The negative pressure module is communicated with the pressure chamber. Each of the wells is for containing a liquid, the negative pressure module is for generating a negative pressure in the pressure chamber, so as to drive the liquid in each of the wells to pass through the hole, and the liquid forms a hanging drop hanging from the bottom surface of the cover.

13 Claims, 18 Drawing Sheets
(7 of 18 Drawing Sheet(s) Filed in Color)

HANGING DROP DEVICE, FORMATION METHOD OF HANGING DROP AND CELL CULTURE METHOD BY USING HANGING DROP

CROSS REFERENCE TO RELATED APPLICATIONS

This application claims priority to Taiwan Application Serial Number 110106799, filed Feb. 25, 2021, which is herein incorporated by reference.

BACKGROUND

Technical Field

The present disclosure relates to a cell culture device. More particularly, the present disclosure relates to a hanging drop device which is for forming hanging drops through air pressure change.

Description of Related Art

The conventional cell culture technique is to culture cells on two-dimensional planes, such as a petri dish. However, the two-dimensional culture environment has a huge difference from the three-dimensional environment in vivo, which results in incomplete physiological expressions of cells. In order to simulate the three-dimensional growing environment, various three-dimensional culture techniques are developed. For example, cells can be cultured on three-dimensional structures, such as scaffolds or hydrogels. Suspension method or hanging drop method can also be adopted.

In hanging drop method, drops hanging from a surface are first formed, and then cells are cultured in the drops. The conventional hanging drop plate includes a plurality of through holes, and the through holes extend from an upper surface to a bottom surface of the hanging drop plate. Users can use pipette to add liquid into the through holes from the upper surface of the hanging drop plate. When the liquid reaches the bottom surface of the hanging drop plate, the liquid becomes hanging drops hanging from the bottom surface due to the action of surface tension. As using the conventional hanging drop plate to form the hanging drops, the liquid should be added one by one with the pipette, which is an extremely labor-intensive and time-consuming process.

Furthermore, devices with pipetting system or microfluidic system, which helps hanging drops formation, are appeared in the market. Liquid can be added into multiple through holes by the pipetting system simultaneously, so as to form a large number of hanging drops at a time. However, the pipetting system is quite expensive. The number and position of through holes which are correspondingly filled by the pipetting system are fixed, and there is no room for adjustment when using the pipetting system. The microfluidic system has a channel communicating with each through hole. When liquid is added into the channel, hanging drops can be formed depending on the pressure of the liquid. Nevertheless, contamination is likely to occur between different hanging drops because the liquid flows through every through hole, which is undesirable for further experiments such as drug tests.

In this regard, it is still an unsolved problem to enhance the convenience and efficiency of forming hanging drops, as well as to maintain the separation of hanging drops without over cost.

SUMMARY

According to one aspect of the present disclosure, a hanging drop device includes a hanging drop box and a negative pressure module. The hanging drop box includes a plate and a cover, and the cover is coupled with the plate to jointly delimit a pressure chamber. The cover includes an upper surface and a bottom surface opposite to the upper surface, a plurality of wells are recessed from the upper surface, and each of the plurality of wells is communicated with the pressure chamber through a hole. The negative pressure module is communicated with the pressure chamber. Each of the plurality of wells is configured for containing a liquid, the negative pressure module is configured for generating a negative pressure in the pressure chamber, so as to drive the liquid in each of the plurality of wells to pass through the hole, and the liquid forms a hanging drop hanging from the bottom surface of the cover.

According to another aspect of the present disclosure, a formation method of a hanging drop includes steps as follows. A hanging drop device of the aforementioned aspect is provided, a filling step is performed and a pressure reducing step is performed. In the filling step, the liquid is added onto the cover of the hanging drop box, so as to fill the plurality of wells of the cover with the liquid. In the pressure reducing step, a negative pressure environment is formed within the pressure chamber in the hanging drop box with the negative pressure module, so as to drive the liquid in each of the plurality of wells to pass through the hole, and the liquid forms the hanging drop hanging from the bottom surface of the cover.

According to one another aspect of the present disclosure, a cell culture method by using a hanging drop includes steps as follows. A hanging drop device of the aforementioned aspect is provided, a filling step is performed, a pressure reducing step is performed and a culturing step is performed. In the filling step, a culture medium is added onto the cover of the hanging drop box, so as to fill the plurality of wells of the cover with the culture medium, and the culture medium includes a plurality of cells. In the pressure reducing step, a negative pressure environment is formed within the pressure chamber in the hanging drop box with the negative pressure module, so as to drive the culture medium in each of the plurality of wells to pass through the hole, and the culture medium forms the hanging drop hanging from the bottom surface of the cover. In the culturing step, the hanging drops are cultured.

BRIEF DESCRIPTION OF THE DRAWINGS

The patent or application file contains at least one drawing executed in color. Copies of this patent or patent application publication with color drawing(s) will be provided by Office upon request and payment of the necessary fee. The present disclosure can be more fully understood by reading the following detailed description of the embodiment, with reference made to the accompanying drawings as follows.

DETAILED DESCRIPTION

Figure 1:
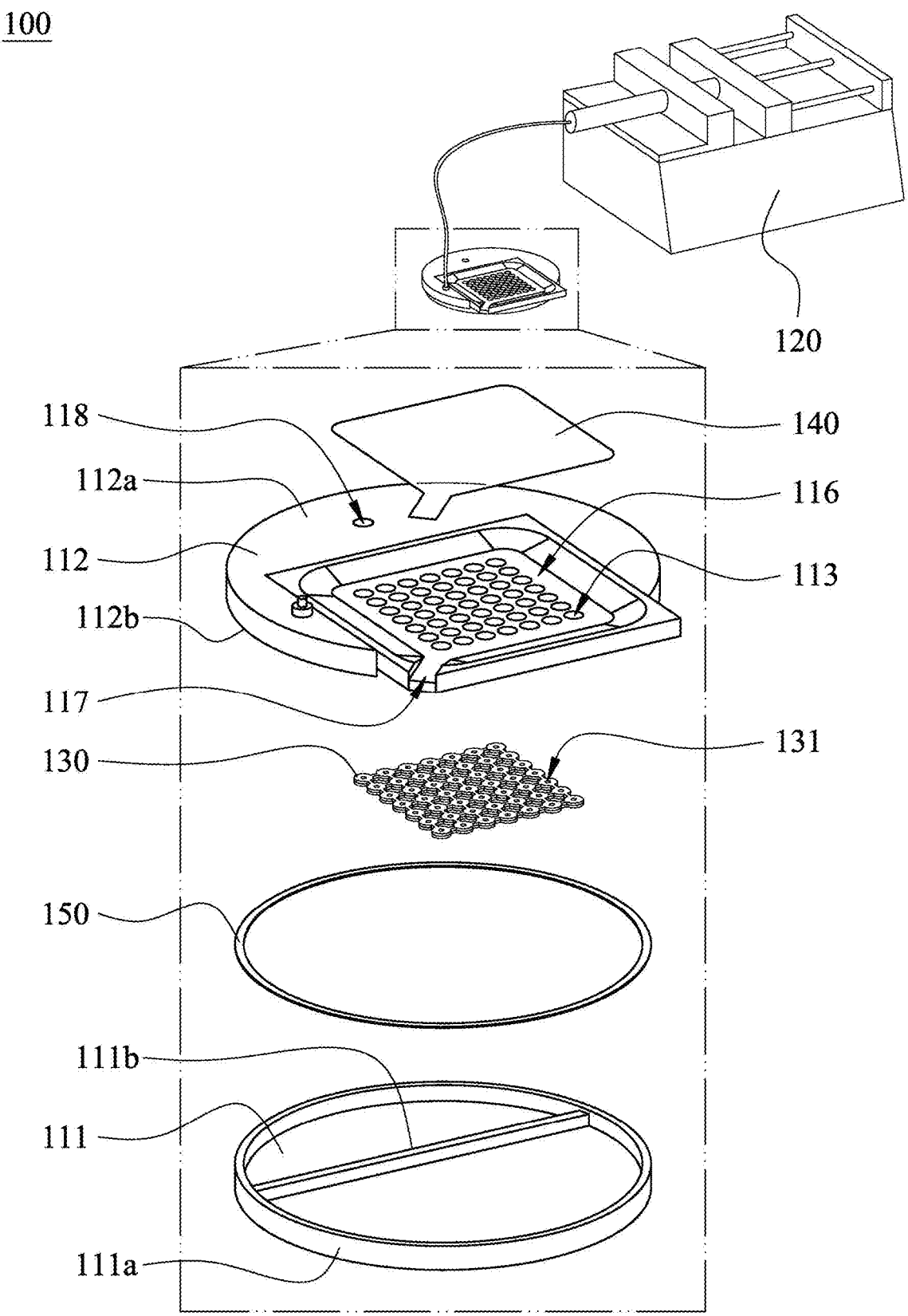
FIG. 1 is an explosive schematic view of a hanging drop device according to an embodiment of one aspect in the present disclosure.
Figure 2:
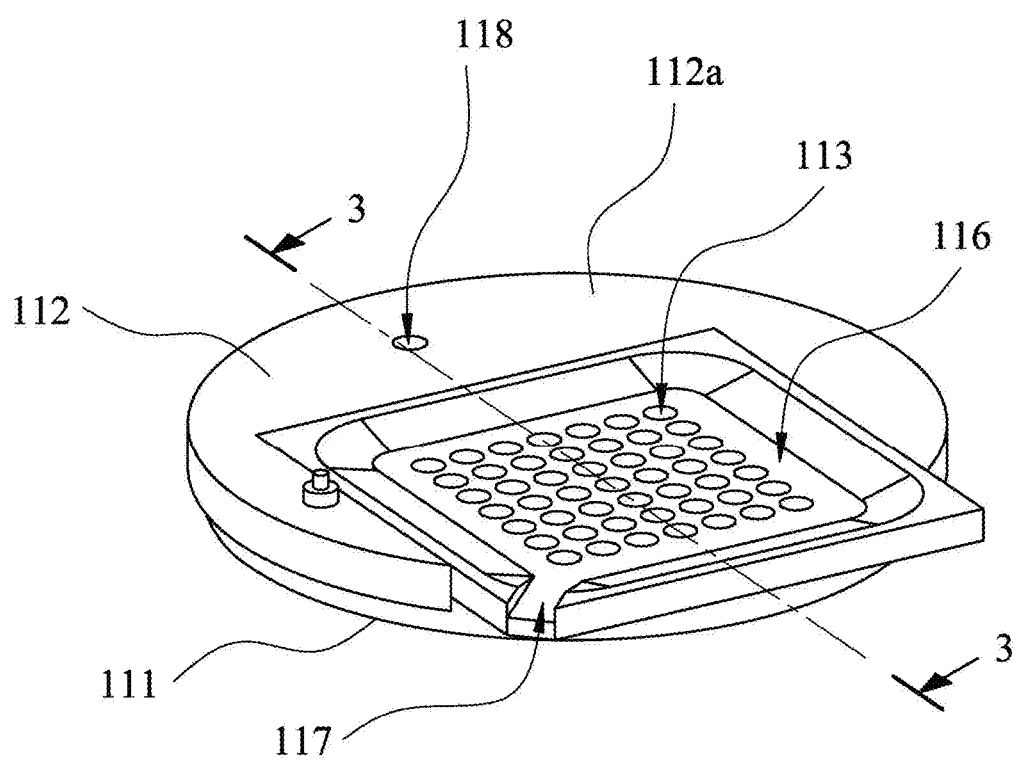
FIG. 2 is a three-dimensional schematic view of a hanging drop box of the hanging drop device of FIG. 1.
Figure 3:
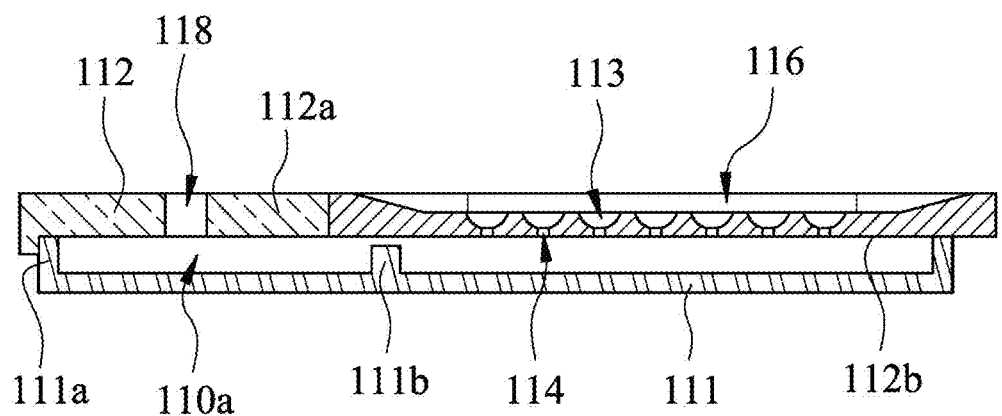
FIG. 3 is a cross-sectional schematic view along line 3-3 of the hanging drop box of FIG. 2.

Please refer to FIG. 1 to FIG. 3. FIG. 1 is an explosive schematic view of a hanging drop device 100 according to an embodiment of one aspect in the present disclosure. FIG. 2 is a three-dimensional schematic view of a hanging drop box 110 of the hanging drop device 100 of FIG. 1. FIG. 3 is a cross-sectional schematic view along line 3-3 of the hanging drop box 110 of FIG. 2. The hanging drop device 100 includes the hanging drop box 110 and a negative pressure module 120. The hanging drop box 110 includes a pressure chamber 110a. The negative pressure module 120 is communicated with the pressure chamber 110a and configured for generating a negative pressure in the pressure chamber 110a.

The hanging drop box 110 includes a plate 111 and a cover 112, and the cover 112 is coupled with the plate 111 to jointly delimit the pressure chamber 110a. The cover 112 includes an upper surface 112a and a bottom surface 112b opposite to the upper surface 112a. A plurality of wells 113, which are configured for containing liquid that will form hanging drops, are recessed from the upper surface 112a. Each of the wells 113 is communicated with the pressure chamber 110a through a hole 114. When the pressure in the pressure chamber 110a is negative, the liquid in each of the wells 113 can be driven to pass through the hole 114 and form a hanging drop hanging from the bottom surface 112b of the cover 112.

Figure 4A:
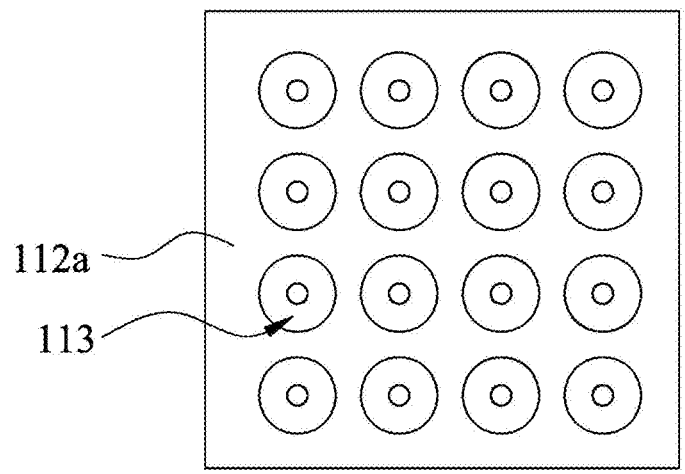
FIG. 4A is an upper schematic view of wells of the hanging drop box being arranged in a rectangular array.

Please refer to FIG. 4A. FIG. 4A is an upper schematic view of the wells 113 of the hanging drop box 110 being arranged in a rectangular array. The wells 113 can be arranged in a rectangular array on the upper surface 112a of the cover 112. This arrangement is relatively simple and is convenient for design and manufacture. Further, more wells 113 can be disposed in the same area, so as to increase the hanging drop density.

Figure 4B:
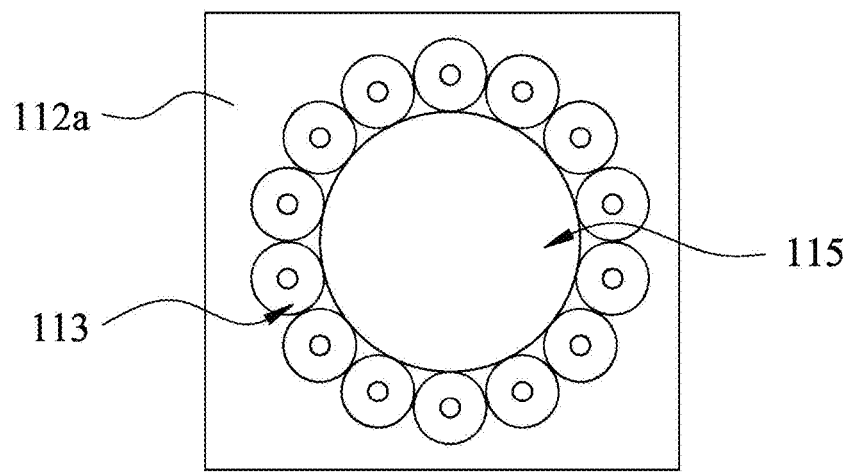
FIG. 4B is an upper schematic view of the wells of the hanging drop box being arranged in a circular arrangement.

Please refer to FIG. 4B. FIG. 4B is an upper schematic view of the wells 113 of the hanging drop box 110 being arranged in a circular arrangement. The wells 113 can be arranged in a circular arrangement on the upper surface 112a of the cover 112. A liquid gathering portion 115 can be recessed from the upper surface 112a, and the wells 113 are arranged around the liquid gathering portion 115. By arranging the liquid gathering portion 115, the efficiency of filling or removing excess liquid can be enhanced. The detailed operation will be introduced in the following paragraphs, and the details will not be given herein.

Figure 5:
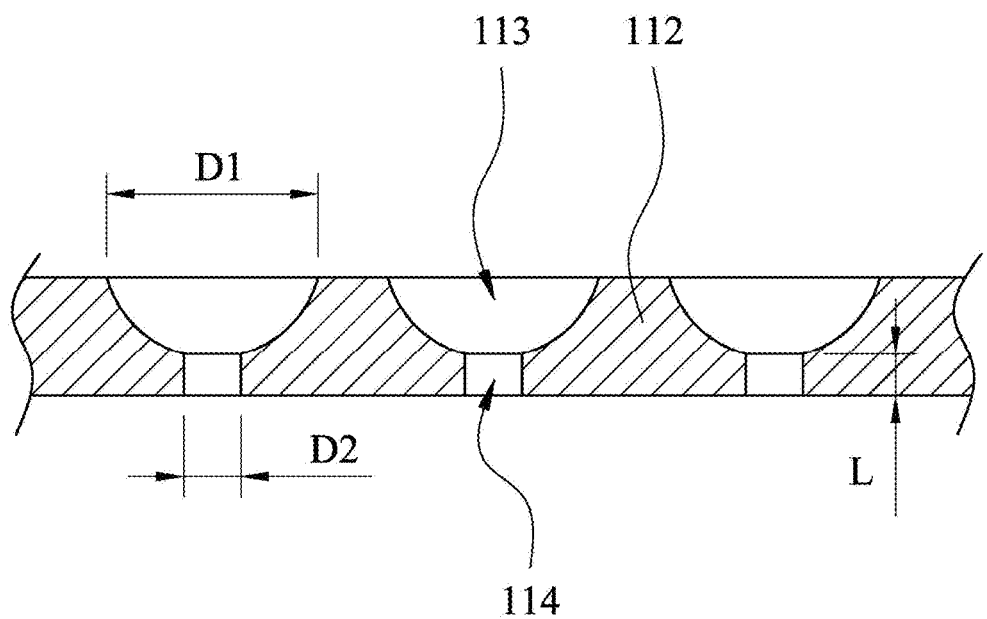
FIG. 5 is a partial cross-sectional schematic view of a cover of the hanging drop box.

Sizes of the wells 113 and the holes 114 will affect the formation ratio of the hanging drops. Please refer to FIG. 5. FIG. 5 is a partial cross-sectional schematic view of the cover 112 of the hanging drop box 110. Each of the wells 113 can be in a semi-spherical form, and a diameter D1 thereof can be 1-8 mm. Thus, the hanging drops will be formed with suitable sizes for cells to grow, and the fall of hanging drops due to the large sizes is prevented. A diameter D2 of each of the holes 114 can be 0.5-2 mm, and an axial length L of each of the holes 114 can be 0.5-5 mm. The liquid can easily pass through the holes 114 under a negative pressure condition, and it makes sure that the hanging drops do not shrink back into the holes 114 as the pressure returns to standard atmosphere. Therefore, the formation ratio of the hanging drops can be enhanced by arranging the wells 113 and the holes 114 with specific sizes.

Please refer to FIG. 1. The cover 112 can further include a concave portion 116 and a liquid exiting channel 117. The concave portion 116 and the liquid exiting channel 117 are both recessed from the upper surface 112a. The wells 113 are arranged at the concave portion 116. The liquid exiting channel 117 is communicated with the concave portion 116, and is configured for draining off the excess liquid in the concave portion 116. By arranging the concave portion 116 and the liquid exiting channel 117, the flow direction of the liquid can be led, which enhances the convenience of filling or draining off liquid.

The negative pressure module 120 makes the negative pressure be generated by moving out the air in the pressure chamber 110a. Thus, the negative pressure module 120 can be a pump, which is favorable for controlling the air extraction rate and the negative pressure in the pressure chamber 110a. Also, the negative pressure module 120 can merely be a syringe, and the hanging drops are formed rapidly through manual extraction. The present disclosure is not limited to the type of the negative pressure module 120.

The hanging drop device 100 can further include an attaching film 130 arranged at the bottom surface 112b of the cover 112. The attaching film 130 includes a plurality of through holes 131, and the through holes 131 are respectively corresponding to and communicated with the holes 114. Because the hanging drops will touch the attaching film 130, the attaching film 130 can be made of relatively hydrophilic materials, such as polyethylene terephthalate (PET). Therefore, the affinity between the hanging drops and the attaching film 130 is enhanced, so as to help the hanging drops hang from the cover 112. However, the present disclosure is not limited thereto.

Figure 6A:
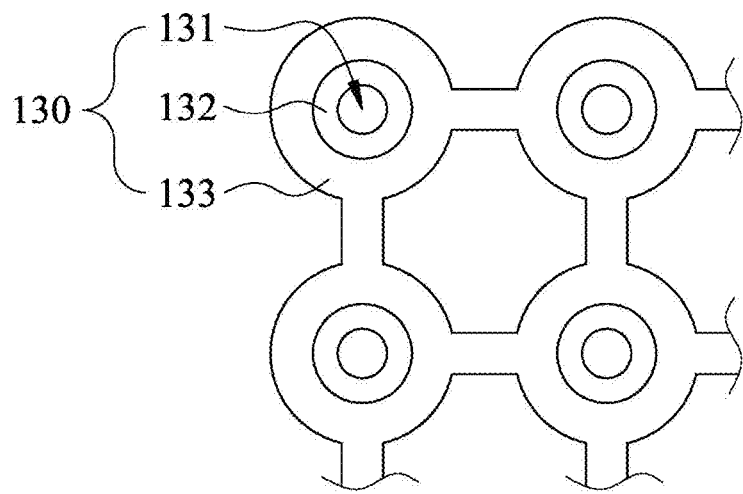
FIG. 6A is a partial bottom schematic view of an attaching film of the hanging drop device.
Figure 6B:
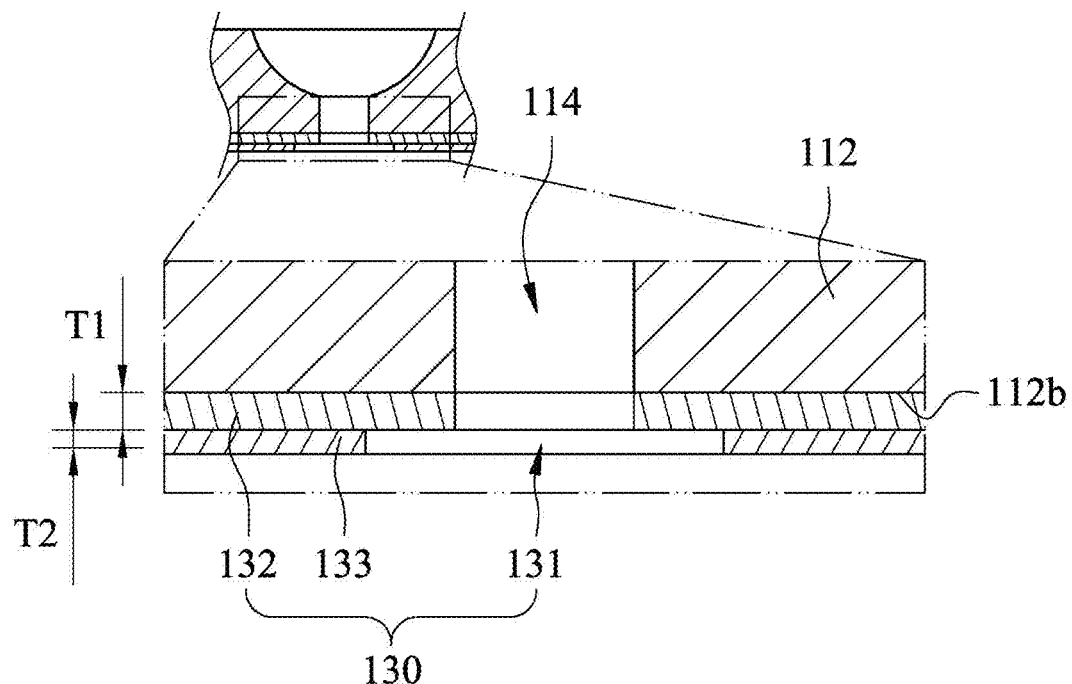
FIG. 6B is a partial cross-sectional schematic view of the cover and the attaching film near holes of the hanging drop box.

Please refer to FIG. 6A and FIG. 6B. FIG. 6A is a partial bottom schematic view of the attaching film 130 of the hanging drop device 100. FIG. 6B is a partial cross-sectional schematic view of the cover 112 and the attaching film 130 near the holes 114 of the hanging drop box 110. The attaching film 130 can be divided into an upper layer 132 and a bottom layer 133. A side edge of the upper layer 132 and the bottom layer 133 surrounding and away from each of the holes 114 is flush. The upper layer 132 and the bottom layer 133 have a first thickness T1 and a second thickness T2 adjacent to each of the holes 114, respectively. The first thickness T1 can be 0.1-1 mm, and the second thickness T2 can be 0.1-1 mm. The first thickness T1 and the second thickness T2 can respectively be 0.25 mm and 0.1 mm, and the attaching film 130 will become an upside down L shape as shown in FIG. 6B. Thus, it prevents the hanging drops from being flat on the surface of the attaching film 130, and is favorable for maintaining the shape of the hanging drops.

Please refer to FIG. 1 and FIG. 3. The plate 111 can include a peripheral wall 111a and a stop portion 111b, and the stop portion 111b is connected to the peripheral wall 111a to divide the plate 111 into two regions. The cover 112 can further include a water inlet 118, the water inlet 118 is corresponding to one of the two regions, and the holes 114 are corresponding to the other one of the two regions. When the hanging drops are formed, water can be added into the one region through the water inlet 118, so as to increase the humidity in the pressure chamber 110a and reduce the evaporation rate of the hanging drops. Through arranging the stop portion 111b, it makes sure that the other one region remains dry, which reduces the possibility of the hanging drops being contaminated.

The hanging drop device 100 can further include an anti-evaporation film 140 which is attached to the upper surface 112a of the cover 112 to close the wells 113. In this regard, the liquid evaporating from the wells 113 is decreased, so as to reduce the evaporation rate of the hanging drops and remain the amount of liquid in the hanging drops.

The hanging drop device 100 can further include a seal ring 150, which is arranged between the cover 112 and the plate 111. The seal ring 150 is configured for sealing the gap between the cover 112 and the plate 111, which prevents air from flowing into the pressure chamber 110a. Therefore, it ensures that the negative pressure in the pressure chamber 110a remains and the formation ratio of the hanging drops is enhanced.

Figure 7:
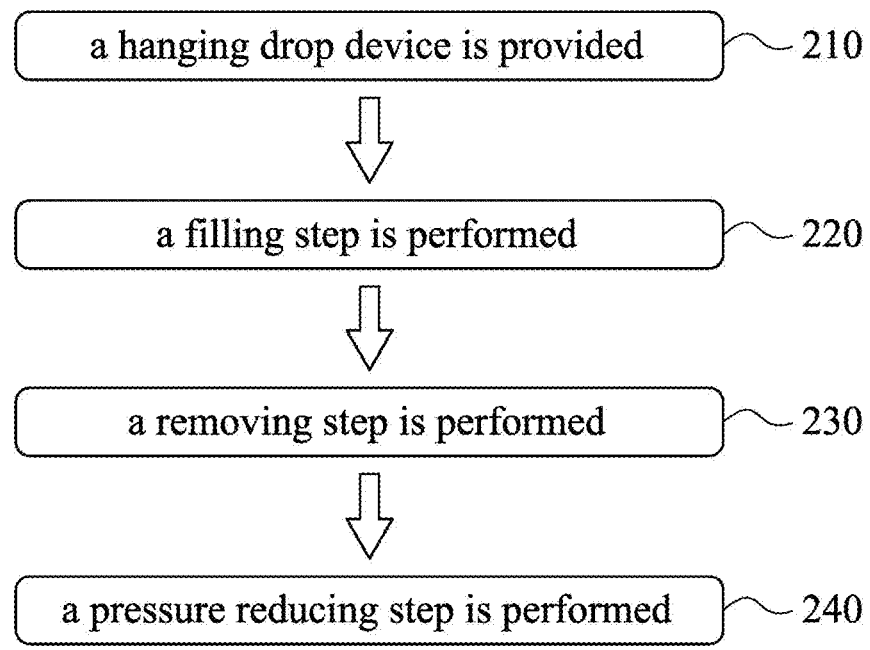
FIG. 7 is a flow chart of a formation method of a hanging drop according to an embodiment of another aspect in the present disclosure.

Please refer to FIG. 7. FIG. 7 is a flow chart of a formation method of a hanging drop 200 according to an embodiment of another aspect in the present disclosure. The formation method of the hanging drop 200 includes Step 210, Step 220, Step 230 and Step 240.

In Step 210, the aforementioned hanging drop device 100 is provided. In Step 220, a filling step is performed by adding a liquid onto the cover 112 of the hanging drop box 110, so as to fill the wells 113 of the cover 112 with the liquid. In Step 230, a removing step is performed to remove the excess liquid from the cover 112.

Figure 8:
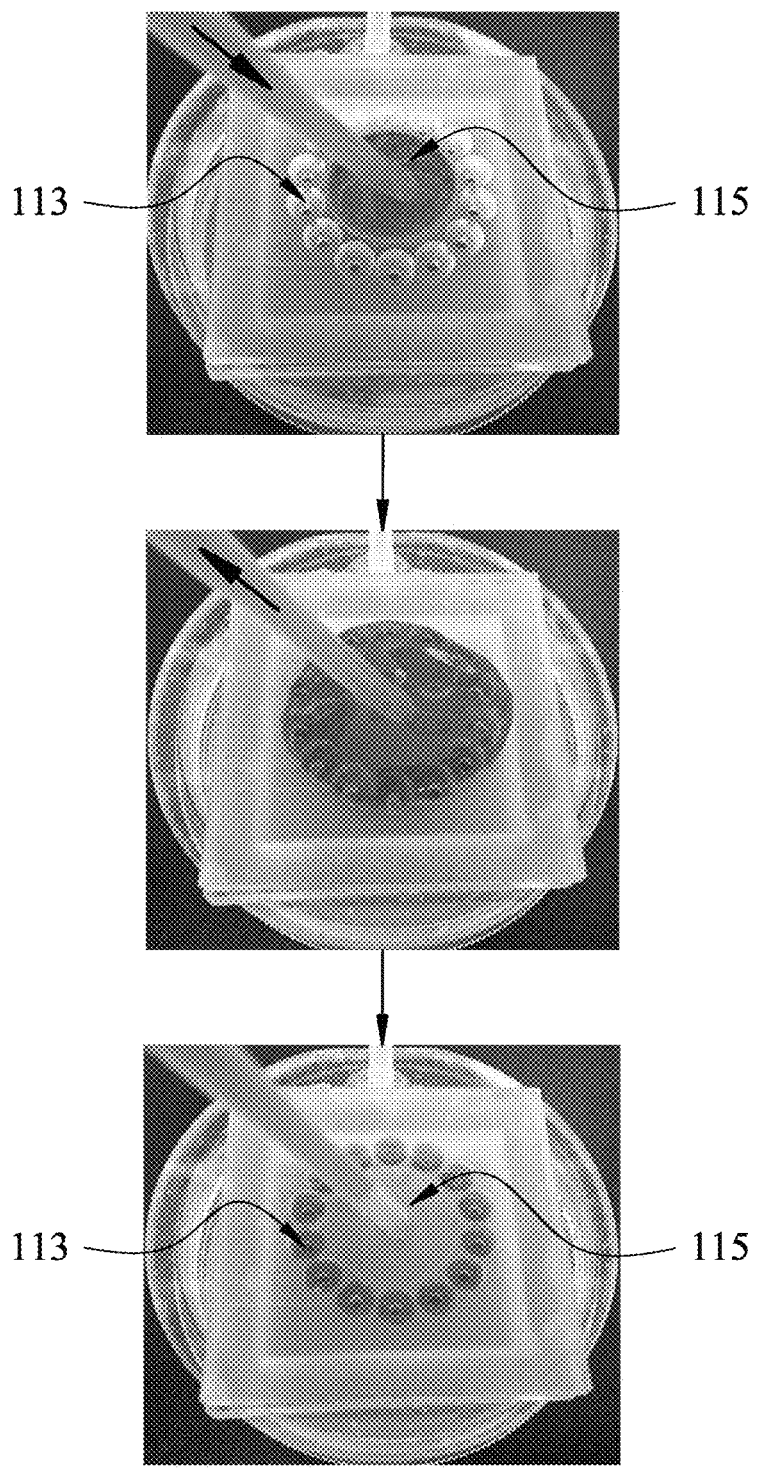
FIG. 8 is a schematic view of filling the hanging drop device of FIG. 4B.

Please refer to FIG. 1. If the hanging drop box 110 includes the concave portion 116 and the liquid exiting channel 117 on the cover 112, the liquid can be added into the concave portion 116 when filling with the liquid. After the liquid enters each of the wells 113, a scraper is used to scrape the excess liquid in the concave portion 116 off through the liquid exiting channel 117. On the other hand, please refer to FIG. 4B and FIG. 8. FIG. 8 is a schematic view of filling the hanging drop device 100 of FIG. 4B. If the hanging drop box 110 includes the wells 113 arranged in the circular arrangement and the liquid gathering portion 115 on the cover 112, the liquid can be continuously added into the liquid gathering portion 115 as filling. The liquid will flow out from the liquid gathering portion 115 and toward the surrounding wells 113. After each of the wells 113 is filled with the liquid, the excess liquid on the cover 112 can be sucked out from the liquid gathering portion 115. The filling process is fast and relatively simple as operating.

Figure 9A:
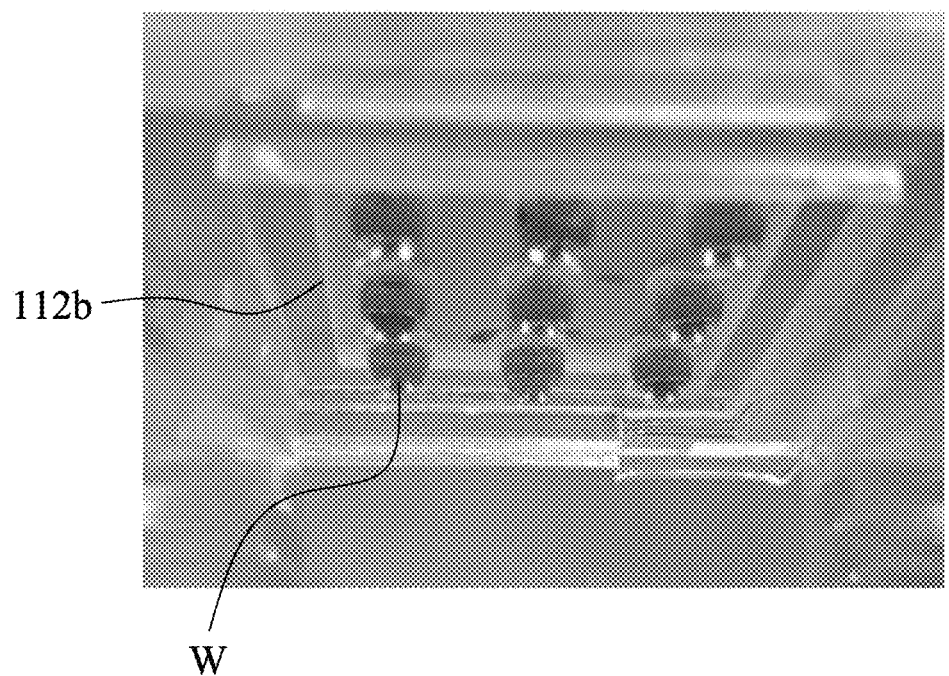
FIG. 9A is a schematic view of the hanging drop device with 9 wells forming hanging drops.
Figure 9B:
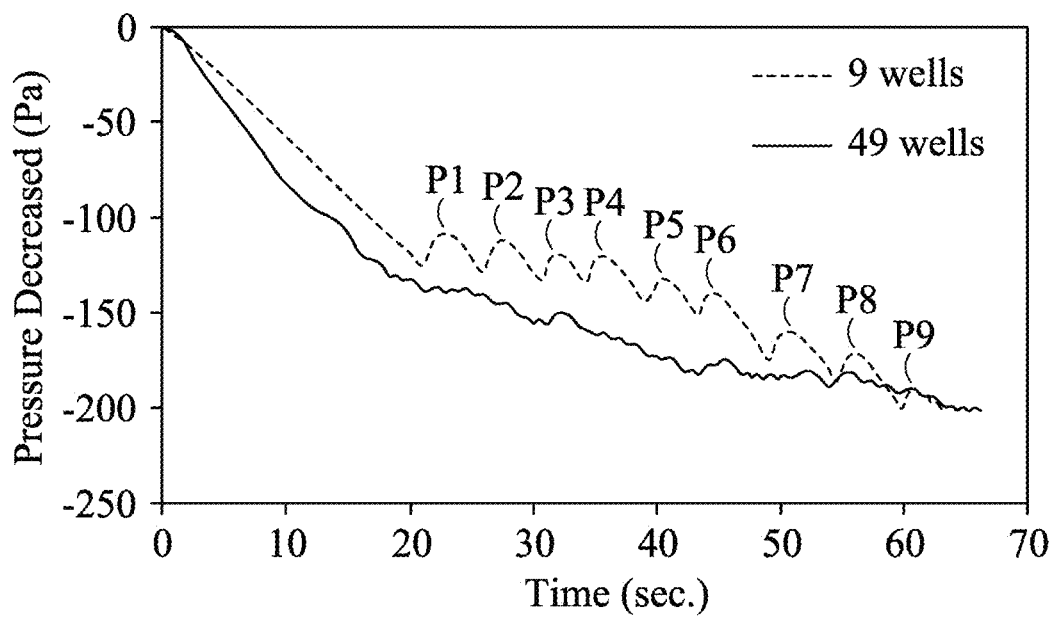
FIG. 9B is a pressure change diagram of the hanging drop device with different number of wells forming hanging drops.

Please refer to FIG. 7 and FIG. 9A. FIG. 9A is a schematic view of the hanging drop device 100 with 9 wells 113 forming hanging drops. In Step 240, a pressure reducing step is performed. A negative pressure environment is formed within the pressure chamber 110a in the hanging drop box 110 with the negative pressure module 120, and a pressure difference forms between the inside and the outside of the hanging drop box 110. Therefore, the liquid in each of the wells 113 is driven to pass through the hole 114. When the liquid reaches the bottom surface 112b of the cover 112, the liquid forms the hanging drop W hanging from the bottom surface 112b due to surface tension. Please refer to FIG. 9B. FIG. 9B is a pressure change diagram of the hanging drop device 100 with different number of wells 113 forming hanging drops. In the pressure reducing step, the pressure within the pressure chamber 110a continuously drops and increases slightly when the hanging drop is formed. When the number of the wells 113 is relatively small, one pressure peak appears as one hanging drop formed. Thus, in FIG. 9B, the pressure change curve of the hanging drop device 100 with 9 wells 113 shows 9 pressure peaks (P1-P9) in total. However, the pressure change curve of the hanging drop device 100 with 49 wells 113 only shows little ups and downs.

It is worth noting that, in the pressure reducing step, the pressure of the negative pressure environment in the pressure chamber 110a is decreased by 100-250 Pa, so as to enhance the formation ratio of the hanging drops. If the pressure is not decreased enough, the liquid in the wells 113 is unable to overcome the force of capillary action and pass through the holes 114 to form the hanging drops. If the pressure is decreased too much, the hanging drops will fall because of the excessive pulling force.

Figure 10:
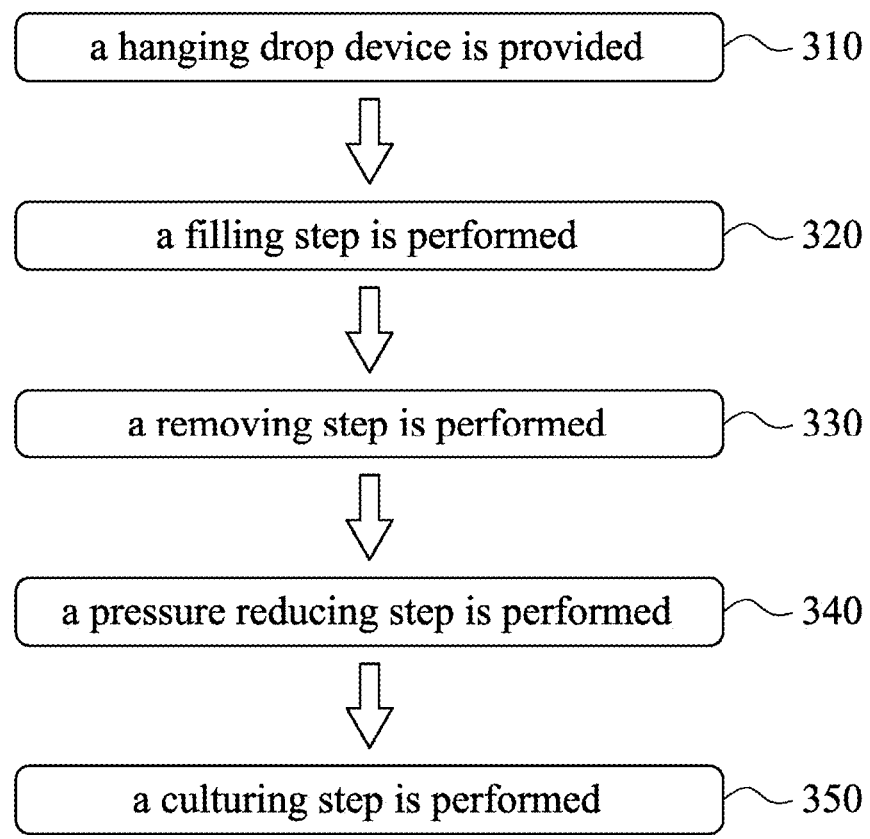
FIG. 10 is a flow chart of a cell culture method by using a hanging drop according to an embodiment of one another aspect in the present disclosure.

Please refer to FIG. 10. FIG. 10 is a flow chart of a cell culture method by using a hanging drop 300 according to an embodiment of one another aspect in the present disclosure. The cell culture method by using the hanging drop 300 includes Step 310, Step 320, Step 330, Step 340 and Step 350. Step 310, Step 320, Step 330 and Step 340 are similar to Step 210, Step 220, Step 230 and Step 240 of the aforementioned formation method of the hanging drop 200, respectively. The difference is that a culture medium including a plurality of cells is utilized in the cell culture method by using the hanging drop 300, and the hanging drops formed includes the cells. A number of cells in each of the hanging drops can be $1$-$1\times10^5$.

In Step 350, a culturing step is performed by culturing the hanging drops formed in Step 310 to Step 340. Because the hanging drops already include the cells, the hanging drop box 110 attached by the hanging drops can be directly put into the incubator. Observation or other tests can be done after the cells gather and become cell spheroids in the hanging drops.

In the following experiments, the cell culture method by using the hanging drop of the present disclosure is adopted for culturing different types of cells, and the cell morphology is observed to identify the culturing status of the cells in the hanging drops.

1. Adenocarcinomic Human Alveolar Basal Epithelial Cells (A549 Cells)

Figure 11A:
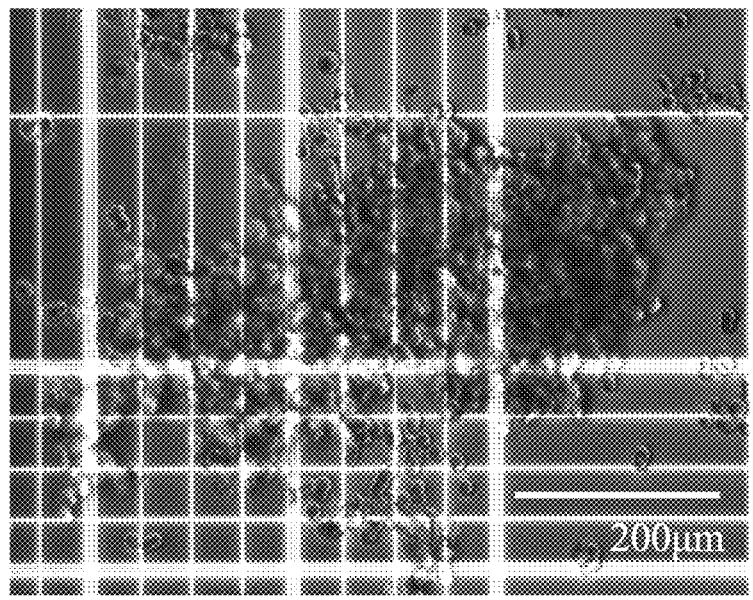
FIG. 11A is a microscope image of A549 cells cultured in the hanging drop for 3 days.
Figure 11B:
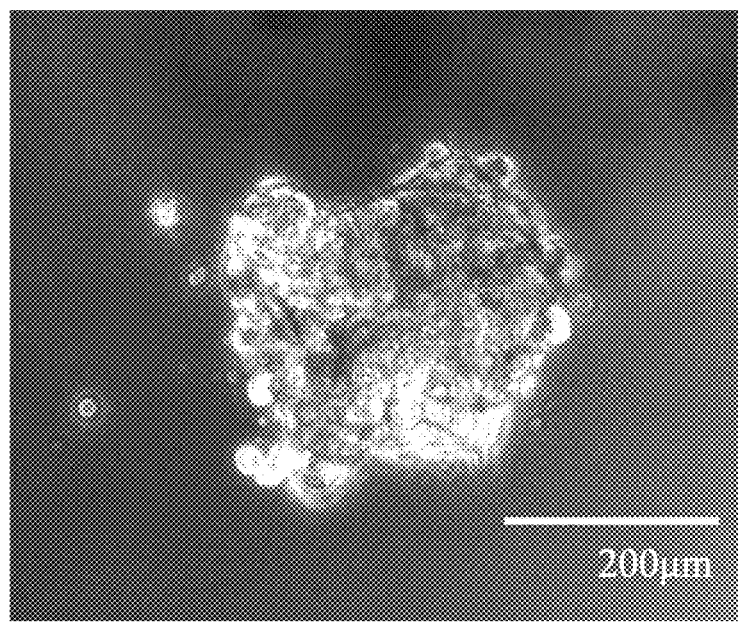
FIG. 11B is a microscope image of A549 cells cultured in the hanging drop for 7 days.

Please refer to FIG. 11A and FIG. 11B. FIG. 11A is a microscope image of A549 cells cultured in the hanging drop for 3 days. FIG. 11B is a microscope image of A549 cells cultured in the hanging drop for 7 days. From the aforementioned microscope images, it can be understood that A549 cells are able to form cell cluster after being cultured in the hanging drop for 3 days, and the cell cluster develops into cell spheroid with irregular shape after 7 days. It proves that A549 cells can successfully grow in the hanging drops formed by the hanging drop device of the present disclosure, and the hanging drops can simulate the three-dimensional environment and make A549 cells become the morphology of cell spheroid.

2. Human Umbilical Cord-Derived Mesenchymal Stem Cells

Figure 12A:
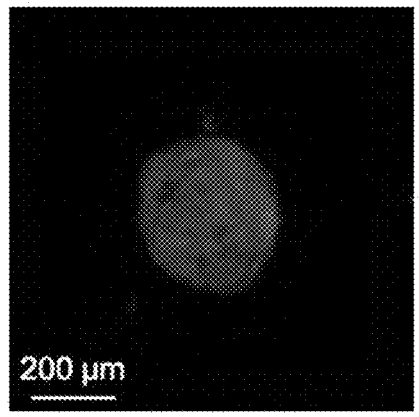
FIG. 12A is a fluorescent microscope image of MSCs cultured in the hanging drop for 1 day.
Figure 12B:
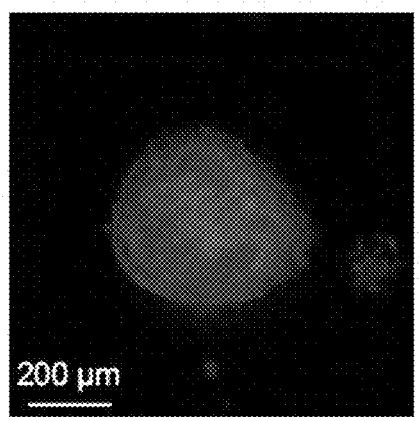
FIG. 12B is a fluorescent microscope image of MSCs cultured in the hanging drop for 2 days.
Figure 12C:
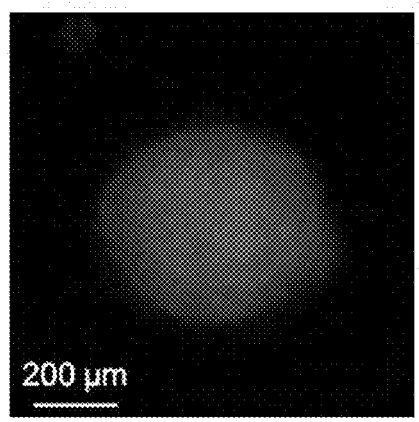
FIG. 12C is a fluorescent microscope image of MSCs cultured in the hanging drop for 3 days.

In the present experiment, human umbilical cord-derived mesenchymal stem cells (MSCs) with red fluorescent protein gene transferred are cultured. Please refer to FIG. 12A to FIG. 12C. FIG. 12A, FIG. 12B and FIG. 12C are fluorescent microscope images of MSCs cultured in the hanging drop for 1, 2 and 3 days, respectively. From the aforementioned microscope images, it can be understood that MSCs can form cell spheroid in the hanging drop. The diameter of the MSCs spheroid is gradually increased as the culturing time passing, which proves that MSCs constantly proliferate in the hanging drop and have great cell viability.

Figure 13A:
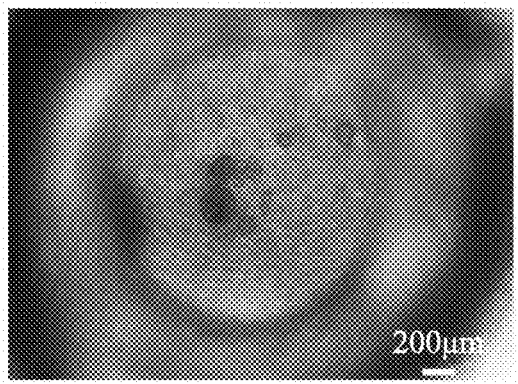
FIG. 13A is a microscope image of HUVECs and MSCs co-cultured in the hanging drop for 1 day.
Figure 14A:
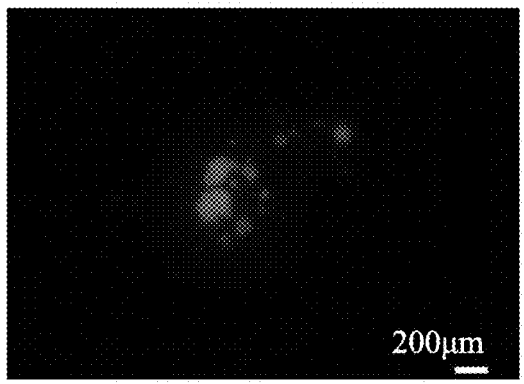
FIG. 14A is a fluorescent microscope image of HUVECs and MSCs co-cultured in the hanging drop for 1 day.
Figure 13B:
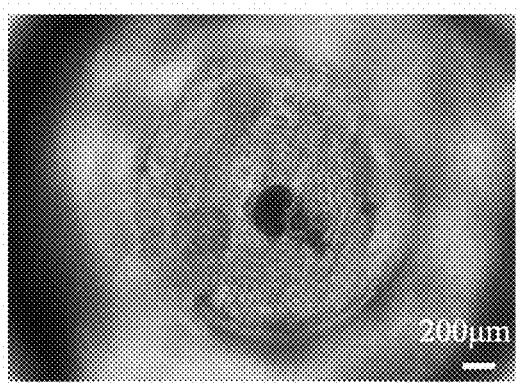
FIG. 13B is a microscope image of HUVECs and MSCs co-cultured in the hanging drop for 2 days.
Figure 14B:
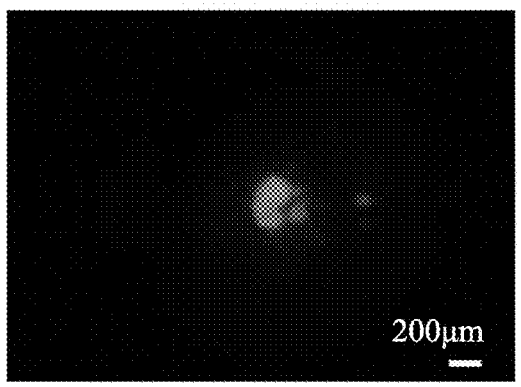
FIG. 14B is a fluorescent microscope image of HUVECs and MSCs co-cultured in the hanging drop for 2 days.
Figure 13C:
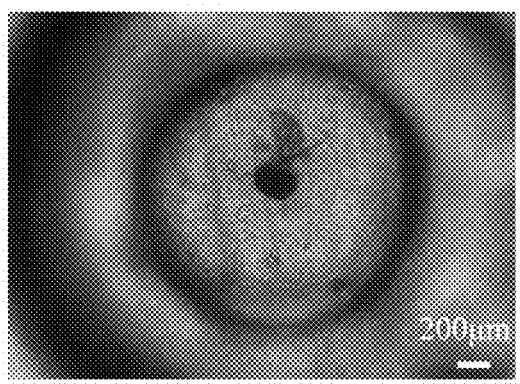
FIG. 13C is a microscope image of HUVECs and MSCs co-cultured in the hanging drop for 3 days.
Figure 14C:
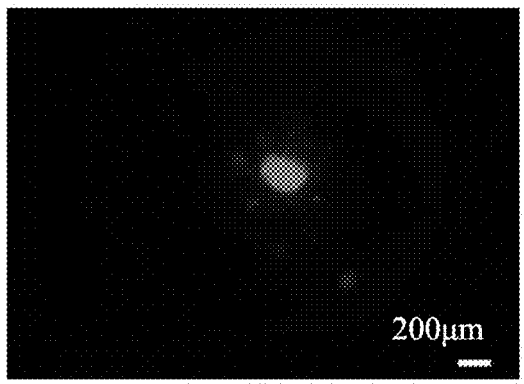
FIG. 14C is a fluorescent microscope image of HUVECs and MSCs co-cultured in the hanging drop for 3 days.

3. Human Umbilical Vein Endothelial Cells and Human Umbilical Cord-Derived Mesenchymal Stem Cells In the present experiment, human umbilical vein endothelial cells (HUVECs) and MSCs are co-cultured. Please refer to FIG. 13A to FIG. 14C. FIG. 13A, FIG. 13B and FIG. 13C are microscope images of HUVECs and MSCs co-cultured in the hanging drop for 1, 2 and 3 days, respectively. FIG. 14A, FIG. 14B and FIG. 14C are fluorescent microscope images of HUVECs and MSCs co-cultured in the hanging drop for 1, 2 and 3 days, respectively. In FIG. 13A and FIG. 14A, cells first grow into several spheroids with smaller volume which are scattered in the hanging drop. As the culturing time passing, the cell spheroids gradually gather and finally become the single spheroid as shown in FIG. 13C and FIG. 14C. Thus, it proves that it is favorable for cell gathering and forming cell spheroid by culturing the cells in the hanging drops formed by the hanging drop device of the present disclosure.

Furthermore, the cells of Experiment 1 to Experiment 3 are all able to form complete cell spheroids in the hanging drops. It proves that the cell culture method by using the hanging drop of the present disclosure is suitable for culturing different types of cells.

4. Fabrication of Three-Dimensional Kidney Microtissues

In the serial experiments, immortalized mouse podocytes with temperature-sensitive T antigen and green fluorescent protein gene transferred and MSCs with red fluorescent protein gene transferred are co-cultured. The ratio of the number of podocytes to the number of MSCs is 1:1.

4-1. Effects on Cell Morphology Due to Different Cell Number

Figure 15:
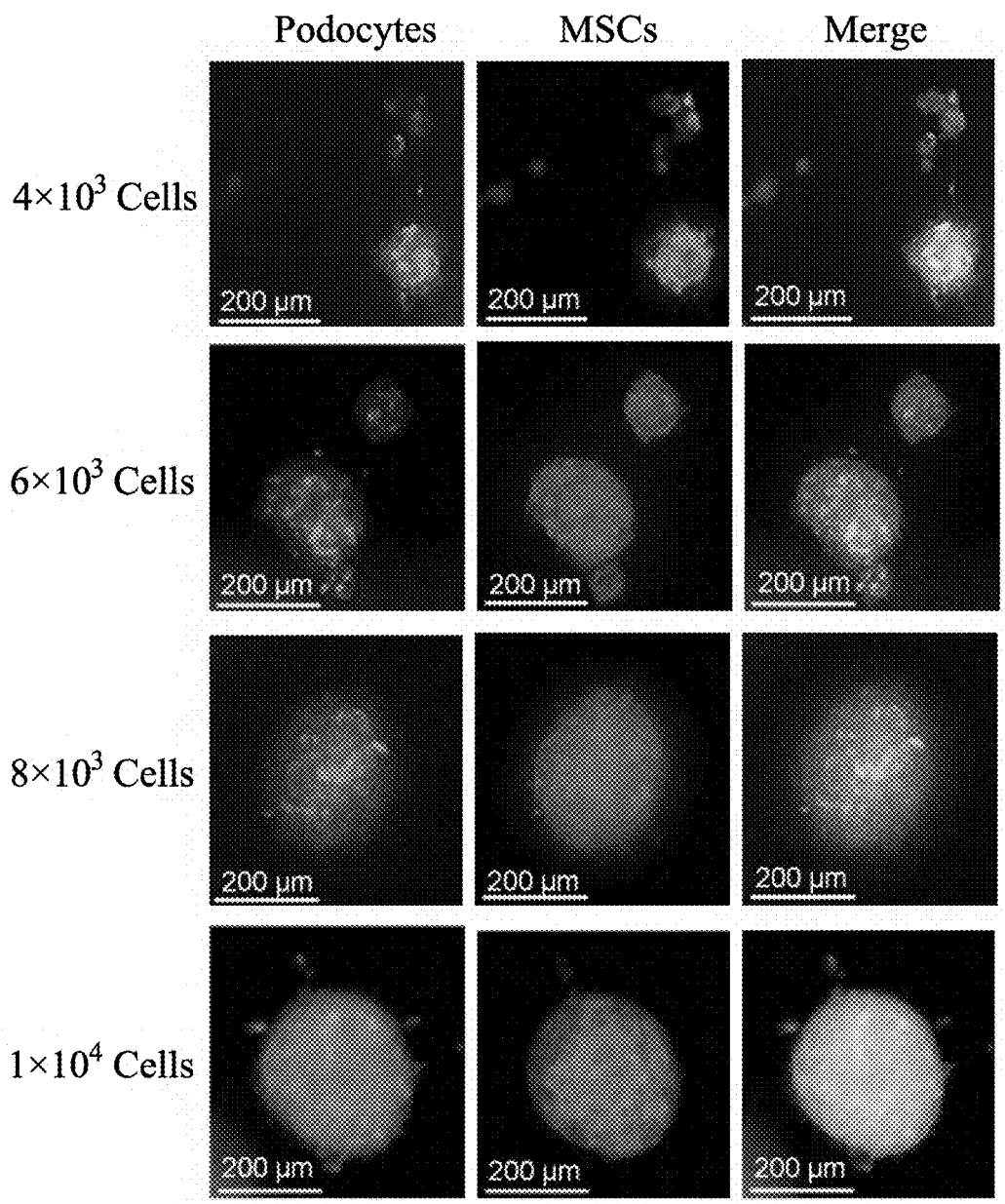
FIG. 15 is a fluorescent microscope image of different number of podocytes and MSCs co-cultured in the hanging drop for 1 day.
Figure 16:
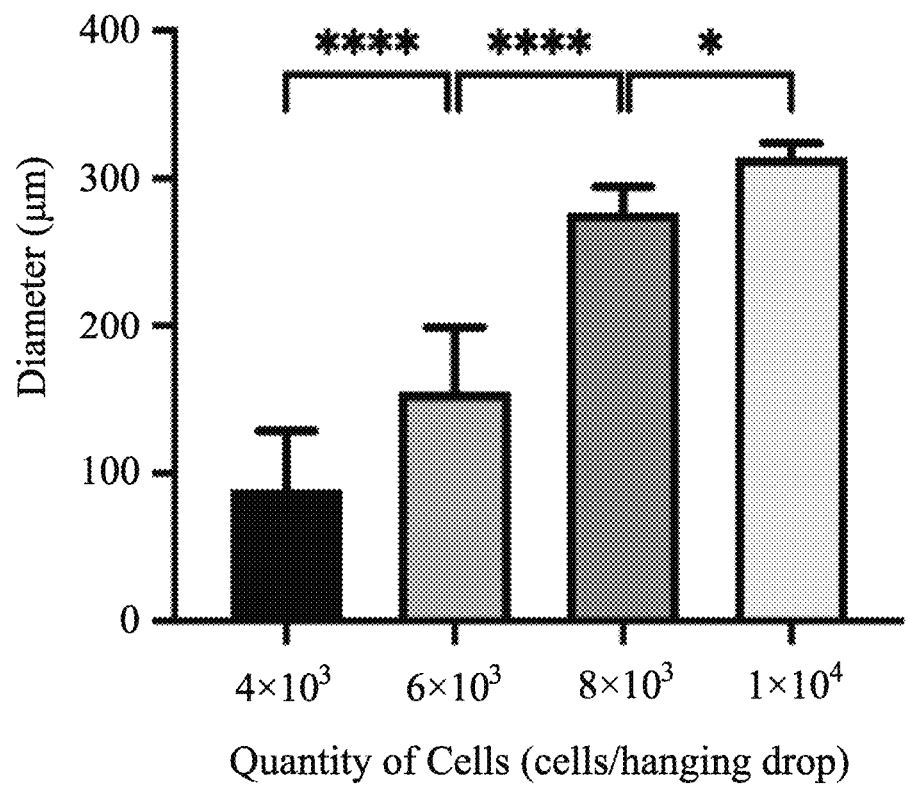
FIG. 16 is a size analysis diagram of cell spheroids formed by different number of podocytes and MSCs co-cultured in the hanging drop for 1 day.

The present experiment is divided into 4 groups, and the number of the cells cultured in every hanging drop of the 4 groups is $4\times10^3$, $6\times10^3$, $8\times10^3$ and $1\times10^4$, respectively. The culturing time is 1 day, and the culturing status with different number of cells is observed. Please refer to FIG. 15 and FIG. 16. FIG. 15 is a fluorescent microscope image of different number of podocytes and MSCs co-cultured in the hanging drop for 1 day. FIG. 16 is a size analysis diagram of cell spheroids formed by different number of podocytes and MSCs co-cultured in the hanging drop for 1 day. In FIG. 15, the cells tend to gather and form multiple cell spheroids when the cell number is less than $6\times10^3$, and the sizes and shapes of the multiple cell spheroids differ. Conversely, the cells can gather and form single cell spheroid when the cell number is more than $8\times10^3$. From the analytic result in FIG. 16, it can be understood that the sizes of the cell spheroids have high consistency, which is favorable for further experiments, such as drug tests. Furthermore, it can be observed that podocytes and MSCs distribute quite evenly in the cell spheroid when the cell number is more than $1\times10^4$. It proves that there is great interaction between podocytes and MSCs, which helps the formation of three-dimensional kidney microtissues.

4-2. Effects on Cell Morphology Due to Different Number of Culturing Days

Figure 17:
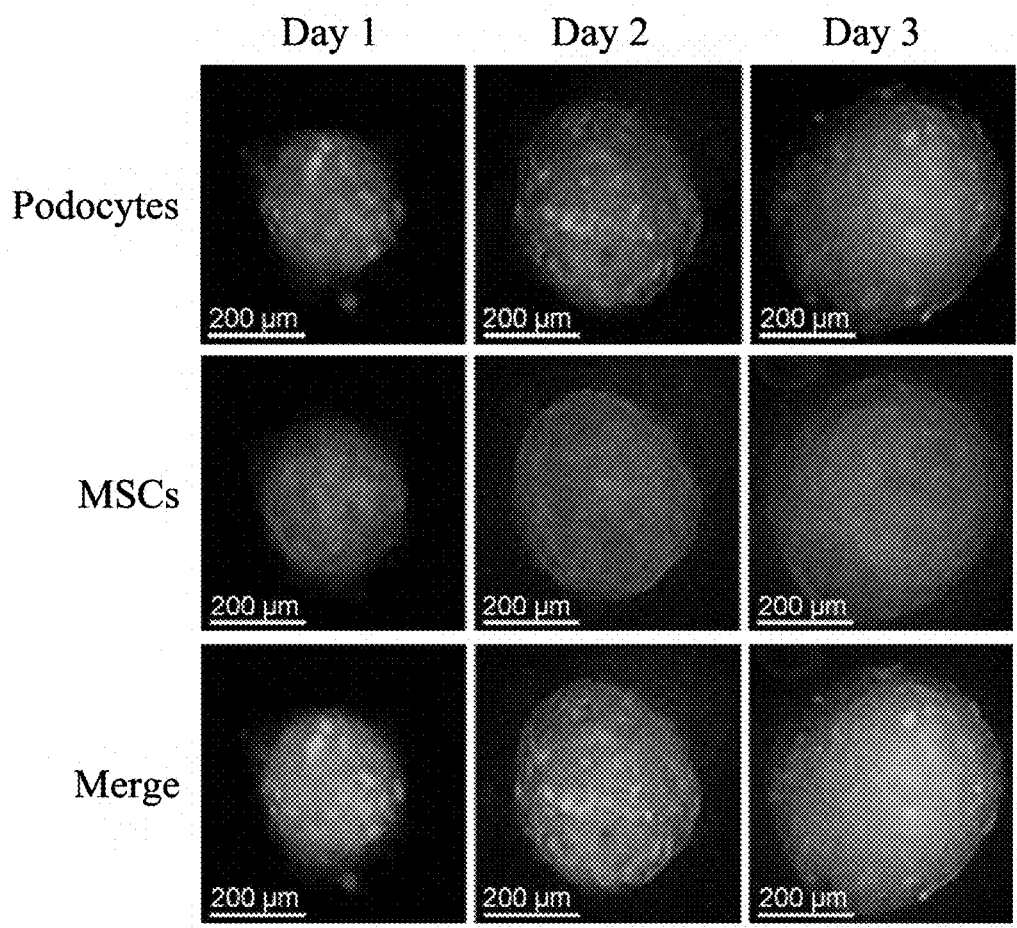
FIG. 17 is a fluorescent microscope image of cell spheroids formed by podocytes and MSCs co-cultured in the hanging drop for different number of culturing days.
Figure 18:
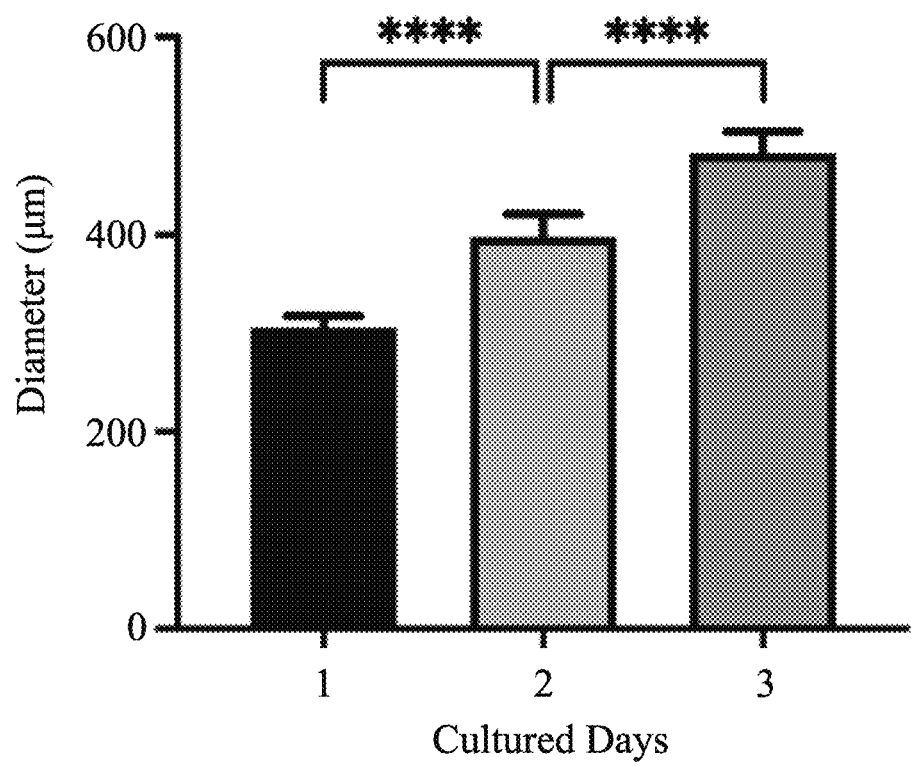
FIG. 18 is a size analysis diagram of the cell spheroids formed by podocytes and MSCs co-cultured in the hanging drop for different number of culturing days.

In the present experiment, cells with the number of $1\times10^4$ are cultured for 1 day to 3 days, and the cell morphology at different culturing day is observed. Please refer to FIG. 17 and FIG. 18. FIG. 17 is a fluorescent microscope image of cell spheroids formed by podocytes and MSCs co-cultured in the hanging drop for different number of culturing days. FIG. 18 is a size analysis diagram of the cell spheroids. As the number of culturing days is increased, the diameter of the cell spheroids is also increased from 300 μm to 500 μm, and podocytes and MSCs distribute quite evenly. It proves that podocytes and MSCs can keep proliferating in the hanging drops formed by the hanging drop device of the present disclosure, and the volume of the cell spheroids is increased.

Figure 19:
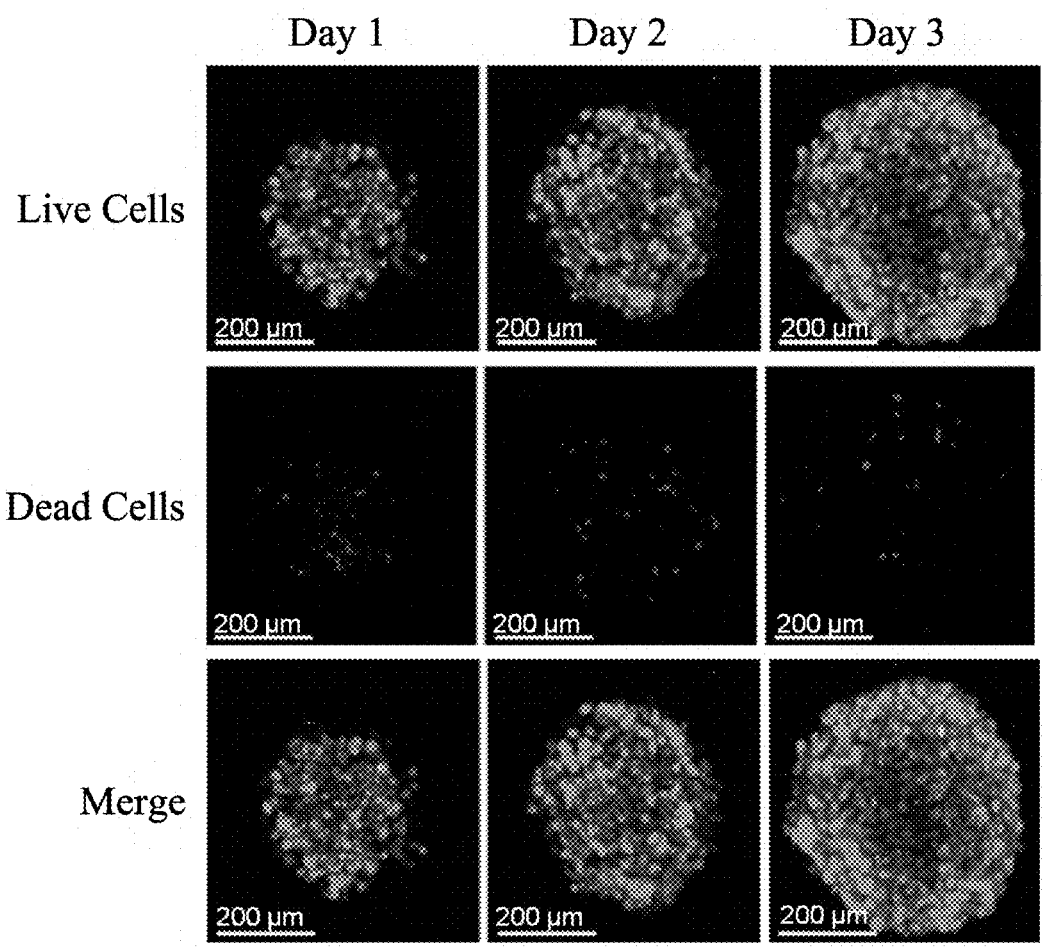
FIG. 19 is a fluorescent microscope image of cell viability test on the cells in the cell spheroids of FIG. 17.

In order to test the viability of cells in the aforementioned cell spheroids, live/dead cell viability assay is taken on the cell spheroids. Please refer to FIG. 19. FIG. 19 is a fluorescent microscope image of cell viability test on the cells in the cell spheroids of FIG. 17. The green fluorescence in FIG. 19 represents live cells, and the red fluorescence represents dead cells. From FIG. 19, it can be understood that the cells in the cell spheroids are mostly live cells during the culturing process, and the massive proliferation does not cause cell death. It proves that the cells cultured in the hanging drops can remain great cell viability.

In this regard, according to the hanging drop device of the present disclosure, a pressure difference forms between the inside and the outside of the pressure chamber by operating the negative pressure module, so as to make the liquid in the wells form the hanging drops rapidly. Thus, it significantly increases convenience and efficiency without excess cost. Moreover, the liquid in each of the wells is not communicated, which makes sure that the hanging drops are independent of one another and the possibility of contamination happening between the hanging drops is reduced.

Although the present disclosure has been described in considerable detail with reference to certain embodiments thereof, other embodiments are possible. Therefore, the spirit and scope of the appended claims should not be limited to the description of the embodiments contained herein.

It will be apparent to those skilled in the art that various modifications and variations can be made to the structure of the present disclosure without departing from the scope or spirit of the disclosure. In view of the foregoing, it is intended that the present disclosure cover modifications and variations of this disclosure provided they fall within the scope of the following claims.

What is claimed is:

1. A hanging drop device, comprising:
a hanging drop box, comprising:
   a plate; and
   a cover coupled with the plate to jointly delimit a pressure chamber, wherein the cover comprises an upper surface and a bottom surface opposite to the upper surface, a plurality of wells are recessed from the upper surface, and each of the plurality of wells is communicated with the pressure chamber through a hole;
a negative pressure module communicated with the pressure chamber; and
an attaching film arranged at the bottom surface of the cover, wherein the attaching film comprises a plurality of through holes, the plurality of through holes are respectively corresponding to and communicated with the holes, and the attaching film is configured for helping a hanging drop hang from the cover;
wherein each of the plurality of wells is configured for containing a liquid, the negative pressure module is configured for generating a negative pressure in the pressure chamber, so as to drive the liquid in each of the plurality of wells to pass through the hole, and the liquid forms the hanging drop hanging from the bottom surface of the cover;
wherein each of the plurality of wells is in a semi-spherical form with a diameter of 1-8 mm, a diameter of each of the holes is 0.5-2 mm, and an axial length of each of the holes is 0.5-5 mm;
wherein each of the holes is in a shape of cylinder, each of the holes comprises a first end and a second end opposite to the first end, the first end is communicated with a corresponding one of the plurality of wells, and the second end is flush with the bottom surface of the cover;
wherein the attaching film is divided into an upper layer and a bottom layer, a side edge of the upper layer and the bottom layer surrounding and away from each of the holes is flush, the upper layer comprises a first thickness adjacent to each of the holes, the bottom layer comprises a second thickness adjacent to each of the holes, the first thickness is 0.25 mm, and the second thickness is 0.1 mm.

2. The hanging drop device of claim 1, wherein the plurality of wells are arranged in a circular form on the upper surface.

3. The hanging drop device of claim 2, wherein a liquid gathering portion is recessed from the upper surface of the cover, and the plurality of wells are arranged around the liquid gathering portion.

4. The hanging drop device of claim 1, wherein the cover further comprises:
a concave portion recessed from the upper surface, wherein the plurality of wells are arranged at the concave portion; and
a liquid exiting channel recessed from the upper surface and communicated with the concave portion, wherein the liquid exiting channel is configured for draining off an excess of the liquid in the concave portion.

5. The hanging drop device of claim 1, wherein the plate comprises a peripheral wall and a stop portion, the stop portion is connected to the peripheral wall to divide the plate into two regions, the cover further comprises a water inlet, the water inlet is corresponding to one of the two regions, and the holes are corresponding to the other one of the two regions.

6. The hanging drop device of claim 1, further comprising an anti-evaporation film attached to the upper surface of the cover to close the plurality of wells, wherein the anti-evaporation film is configured for reducing an evaporation rate of the hanging drop.

7. A formation method of a hanging drop, comprising:
providing a hanging drop device of claim 1;
performing a filling step by adding the liquid onto the cover of the hanging drop box, so as to fill the plurality of wells of the cover with the liquid; and
performing a pressure reducing step by forming a negative pressure environment within the pressure chamber in the hanging drop box with the negative pressure module, a pressure in the pressure chamber is decreased by 100-250 Pa so as to drive the liquid in each of the plurality of wells to pass through the hole, and the liquid forms the hanging drop hanging from the bottom surface of the cover.

8. The formation method of the hanging drop of claim 7, wherein the cover of the hanging drop box further comprises:
a concave portion recessed from the upper surface of the cover, wherein the plurality of wells are arranged at the concave portion; and
a liquid exiting channel recessed from the upper surface of the cover and communicated with the concave portion;
wherein the formation method of the hanging drop further comprises a removing step performed after the filling step, and a scraper is used to scrape an excess of the liquid, which is the liquid overflows from the plurality of wells, in the concave portion off through the liquid exiting channel in the removing step.

9. The formation method of the hanging drop of claim 7, wherein the plurality of wells of the hanging drop box are arranged in a circular form on the upper surface of the cover, a liquid gathering portion is recessed from the upper surface, and the plurality of wells are arranged around the liquid gathering portion;
wherein in the filling step, the liquid is continuously added into the liquid gathering portion until the liquid fills the plurality of wells and then overflows, the formation method of the hanging drop further comprises a removing step performed after the filling step, and an excess of the liquid, which is the liquid overflows from the plurality of wells, on the cover is sucked from the liquid gathering portion in the removing step.

10. A cell culture method by using a hanging drop, comprising:

providing a hanging drop device of claim 1;

performing a filling step by adding a culture medium onto the cover of the hanging drop box, so as to fill the plurality of wells of the cover with the culture medium, and the culture medium comprises a plurality of cells;

performing a pressure reducing step by forming a negative pressure environment within the pressure chamber in the hanging drop box with the negative pressure module, a pressure in the pressure chamber is decreased by 100-250 Pa so as to drive the culture medium in each of the plurality of wells to pass through the hole, and the culture medium forms the hanging drop hanging from the bottom surface of the cover; and performing a culturing step by culturing the hanging drops.

11. The cell culture method by using the hanging drop of claim 10, wherein a number of the plurality of cells in each of the hanging drops is $1-1\times10^5$.

12. The cell culture method by using the hanging drop of claim 10, wherein the cover of the hanging drop box further comprises:

a concave portion recessed from the upper surface of the cover, wherein the plurality of wells are arranged at the concave portion; and a liquid exiting channel recessed from the upper surface of the cover and communicated with the concave portion;

wherein the cell culture method by using the hanging drop further comprises a removing step performed after the filling step, and a scraper is used to scrape an excess of the culture medium, which is the culture medium overflows from the plurality of wells, in the concave portion off through the liquid exiting channel in the removing step.

13. The cell culture method by using the hanging drop of claim 10, wherein the plurality of wells of the hanging drop box are arranged in a circular form on the upper surface of the cover, a liquid gathering portion is recessed from the upper surface, and the plurality of wells are arranged around the liquid gathering portion;

wherein in the filling step, the culture medium is continuously added into the liquid gathering portion until the culture medium fills the plurality of wells and then overflows, the cell culture method by using the hanging drop further comprises a removing step performed after the filling step, and an excess of the culture medium, which is the culture medium overflows from the plurality of wells, on the cover is sucked from the liquid gathering portion in the removing step.

* * * * *